United States Patent [19]

Takao et al.

[11] Patent Number: 5,587,515

[45] Date of Patent: Dec. 24, 1996

[54] METHOD OF MANUFACTURING N-MONOSUBSTITUTED (METH)ACRYLAMIDES

[75] Inventors: Yuuichi Takao; Hidetoshi Oogami, both of Yatsushiro, Japan

[73] Assignee: Kohjin Co., Ltd., Tokyo, Japan

[21] Appl. No.: 256,012

[22] PCT Filed: Oct. 20, 1993

[86] PCT No.: PCT/JP93/01511

§ 371 Date: Jul. 22, 1994

§ 102(e) Date: Jul. 22, 1994

[87] PCT Pub. No.: WO94/08946

PCT Pub. Date: Apr. 28, 1994

[30] Foreign Application Priority Data

Oct. 21, 1992 [JP] Japan ..................................... 4-305860

[51] Int. Cl.$^6$ .................................................. C07C 231/02
[52] U.S. Cl. .......................... 564/135; 564/136; 564/204; 564/205; 562/588
[58] Field of Search ..................................... 564/205, 204, 564/135, 136; 562/588

[56] References Cited

U.S. PATENT DOCUMENTS

| 2,451,436 | 10/1948 | Erickson | 564/205 |
| 3,914,303 | 10/1975 | Daniher et al. | 564/205 |
| 4,044,146 | 8/1977 | Karpati et al. | 424/283 |

FOREIGN PATENT DOCUMENTS

| 54-9170 | 4/1979 | Japan . |
| 58-18346 | 2/1983 | Japan . |
| 4-154749 | 5/1992 | Japan . |
| 4-208258 | 7/1992 | Japan . |

*Primary Examiner*—Shailendra Kumar
*Attorney, Agent, or Firm*—Oliff & Berridge

[57] ABSTRACT

A process for producing N-monosubstituted acrylamides in high yields without forming by-products. The process comprises preparing a β-dialkylamino-(methyl)propionic ester by the reaction of a (meth)-acrylic ester with a specified dialkylamine, converting the formed ester into an N-monosubstituted β-dialkylamino(methyl)propionamide by the reaction thereof with a primary amine in the presence of sodium methoxide, and thermally decomposing the amide under a reduced pressure.

7 Claims, No Drawings

METHOD OF MANUFACTURING N-MONOSUBSTITUTED (METH)ACRYLAMIDES

This application is a 371 of PCT/JP93/01511 filed Oct. 20, 1993.

TECHNICAL FIELD

The present invention relates to an industrially-advantageous method of manufacturing N-monosubstituted (meth-)acrylamides which can be used as a blending agent for concrete, an agent for treating water, a chemical agent for paper, a stabilizer for latex, etc. after being copolymerized with other monomers.

BACKGROUND OF THE ART

With regard to the manufacture of N-monosubstituted (meth)acrylamides, a method involving reacting (meth-)acrylic acid chloride with a primary amine in a neutralizing agent such as sodium hydroxide has been known. However, it is unlikely that said method is industrially advantageous because of the use of expensive materials and neutralizing agents and also the complexity of the operation. On the other hand, in accordance with the reaction of (meth)acrylates with an amines for manufacturing (meth)acrylamides, it is possible to use less expensive materials and, therefore, several methods for the manufacture of N-substituted (meth-)acrylamides by said reaction have been known. Since the double bond in the (meth)acrylates is very reactive, the common means for the manufacture of the desired products in that case is that a protecting group such as an amine, cyclopentadiene, an alcohol, etc. is initially added to the double bond and, after completion of the amidation, the protecting group is detached by heating. For example, the use of cyclopentadiene as a protecting group is disclosed in Examined Japanese Patent Publication (Kokoku) Sho-54/9170, etc. while the use of alcohols as a protective group is disclosed in U.S. Pat. No. 3,914,303, etc.

Further, an example of the use of amines as a protecting group can be found in U.S. Pat. No. 2,451,436 disclosing a method in which an acrylate is made to react with a mono- or dialkylamine and the resulting N-alkyl-beta-alkylaminopropionamide is subjected to thermal decomposition in the presence of an acid to give an N-alkylacrylamide. Another example is Laid-Open Japanese Patent Publication (Koukai) Hei-04/154749 disclosing a method in which N-dimethylamino-beta-dimethylaminopropionamide is subjected to thermal decomposition in a liquid phase to give dimethylacrylamide at a good yield.

In the manufacture of N-substituted (meth)acrylamides using a (meth)acrylate as a starting material, the method using an amine as a protecting group may be industrially advantageous as compared with a method using an alcohol or cyclopentadiene because thermal decomposition in a liquid phase especially at a relatively low temperature is possible. However, though said method has a high yield and is industrially advantageous in the case of the manufacture of N,N-dialkyl(meth)acrylamides, there is a big disadvantage when applying it to the manufacture of N-monosubstituted (meth)acrylamides.

The disadvantage is that the N-monosubstituted beta-amino(methyl)propionamides prepared by the reaction of (meth)acrylates with a primary amine are accompanied by a large amount of impurities having high boiling points and high viscosities which both decrease the yield of the product. In addition, when it is subjected to thermal decomposition to give the desired substance, the boiling point (reaction temperature) becomes higher due to the presence of such highly viscous impurities with high-boiling-points whereby the polymerization of the desired substance is quite apt to take place in such a way so as to result in a further decrease in the yield which, in turn, raises the cost for the purification. In an extreme case, the operation becomes difficult and the expected product cannot be produced.

DISCLOSURE OF THE INVENTION

In order to eliminate such disadvantages, the present inventors have carried out investigations and have found that the desired product can be prepared easily and at a high yield without impurities as by-products in the manufacture of N-monosubstituted beta-amino(methyl)propionic acid amide if two different types of amines—an amine which is added to the double bond of the acryl group and another amine which gives an amide—are used separately and successively in two steps and then the resulting amides are subjected to thermal decomposition whereby the present invention has been achieved.

Thus, the present invention offers an industrially-advantageous method for the manufacture of N-monosubstituted (meth)acrylamide represented by a general formula (1) comprising the following three steps (a) to (c).

$$CH_2=CRCO—NHQ \quad (1)$$

in which R is a hydrogen atom or methyl and Q is an alkyl having 1–12 carbons, a dimethylaminoalkyl having 1–5 carbons or a hydroxyalkyl having 1–3 carbons.

(a): a step in which a (meth)acrylate represented by a general formula (2) is made to react with a dialkylamine represented by a general formula (3) to manufacture a beta-dialkylamino(1-methyl)propionate represented by a general formula (4).

$$CH_2=CRCOOR' \quad (2)$$

in which R is a hydrogen atom or methyl; and R' is a lower alkyl.

$$R^1R^2NH \quad (3)$$

in which $R^1$ and $R^2$ are lower alkyls.

$$R^1R^2N—CH_2—CHRCOOR' \quad (4)$$

in which R is a hydrogen atom or methyl; R' is a lower alkyl; and $R^1$ and $R^2$ are lower alkyls.

(b): a step in which the above-prepared beta-dialkylamino(1-methyl)propionate is made to react with a primary amine represented by a general formula (5) to manufacture an N-monosubstituted beta-dialkylamino(1-methyl)propionamide.

$$NH_2—Q \quad (5)$$

in which Q is an alkyl having 1–12 carbons, a dimethylaminoalkyl having 1–5 carbons or a hydroxyalkyl having 1–3 carbons.

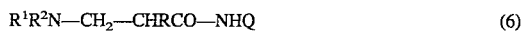

$$R^1R^2N—CH_2—CHRCO—NHQ \quad (6)$$

in which R is a hydrogen atom or methyl; $R^1$ and $R^2$ are lower alkyls; and Q is an alkyl having 1–12 carbons, a dimethylaminoalkyl having 1–5 carbons or a hydroxyalkyl having 1–3 carbons.

(c): a step in which the N-monosubstituted beta-dialkylamino(1-methyl)propionamide is subjected to thermal decomposition to manufacture the desired N-monosubstituted (meth)acrylamide represented by the above-given general formula (1).

In the present invention, examples of the lower alkyl are alkyl groups having 1–3 carbon atoms such as methyl, ethyl, propyl and isopropyl; examples of alkyl groups having 1–12 carbons are methyl, ethyl, propyl, n-butyl, 2-ethylhexyl, n-octyl; an example of a dimethylaminoalkyl group having 1–5 carbons is dimethylaminopropyl; and an example of the hydroxyalkyl having 1–3 carbons is 2-hydroxyethyl.

The present invention will be further illustrated as hereinafter.

Step (a)

This step is carried out by the reaction of (meth)acrylate represented by the general formula (2) with a dialkylamine represented by the general formula (3) under heating.

There is no particular limitation as to the (meth)acrylate used in this step provided that it is an ester with a lower alkyl. However, the use of methyl ester is preferred because its cost is low and the distillation/separation of an alcohol produced as a result of the amidation reaction is easy. With respect to dialkylamine, that which is represented by the general formula (3) may be exemplified, though the use of diethylamine or dipropylamine is particularly preferred. When an alkylamine having butyl or a group having a higher number of carbons is used, the addition reaction to the double bond is difficult to complete as it takes a long time. In addition, the thermal decomposition in step (c) which will be illustrated later is usually carried out in vacuo and, therefore, the use of dimethylamine with a low boiling point is not recommended for an advantageous recovery of the resulting dialkylamine.

The reaction is carried out by mixing 1–2 moles (preferably 1.1–1.3 moles) of dialkylamine with one mole of (meth)acrylate followed by heating the reaction solution at the temperature of the boiling point in the presence of a polymerization inhibitor such as methoxyhydroquinone. The reaction time may be dependent upon the reaction conditions but, usually, it is about from 5 to 24 hours. When an alkali carbonate or the like is used as the catalyst, the reaction proceeds quickly but, in order to suppress the side reactions such as the amidation of the ester and to conduct the reaction in a way that ensures a good yield, it is preferred that no catalyst is used. The reaction may be carried out in the absence of a solvent but, as being found by the present inventors already, it is also possible to accelerate the reaction rate by adding an alcohol (refer to Pending Japanese Patent Application Hei-05/223928).

The compounds represented by the general formula (4) are isolated, after reaction, by removing unreacted dialkylamine and supplied to next process without refining it.

Step (b)

This step is carried out by the reaction of a beta-dialkylamino(1-methyl)propionate represented by the general formula (4) with a primary amine represented by the general formula (5) in the presence of a catalyst.

Examples of the catalyst applicable are alkali metal hydrides and alkali metal alkoxides. The reaction temperature is from 20° to 100° C. (preferably from 30° to 60° C.) while even a reaction time of as short as 1–5 hours is sufficient.

After completion of the reaction, the alkaline catalyst is neutralized by adding sulfuric acid thereto, the salt which is separated out therefrom is filtered off, a polymerization inhibitor is added thereto and the unreacted amine and the alcohol by-product are removed by distillation whereby the compound represented by the general formula (6) can be isolated. This compound may be used without further purification for the next step as well.

Step (c)

This step is carried out by the thermal decomposition of N-monosubstituted beta-dialkylamino(1-methyl)propionamide represented by the general formula (6) in vacuo in the presence of an acid catalyst. Examples of the acid catalyst applicable are sulfuric acid, acrylic acid, etc., while the use of sulfuric acid is preferred. An amount of the acid catalyst of approximately 0.5–2 molar % to the amide represented by the general formula (6) is sufficient. The use of an excessive amount of the acid catalyst is not preferred because it causes side products and polymers to form. Thermal decomposition is carried out in vacuo at a temperature of 100°–200° C. Since the product represented by the general formula (1) is quite polymerizable, the pressure during the operation needs to be preferable enough that said product can be promptly taken out from the reaction system and, moreover, that the by-product dialkylamine can be effectively recovered. Usually, it is from 10 to 200 torr. (For example, in the case of diethlyamine, condensation takes place at −10° C. if the pressure is 40 torr and, therefore, it can be recovered very easily in production.)

After completion of the reaction, the product represented by the general formula (1) can be isolated by distilling the effluent of the thermal decomposition. Most of the residue of the distillation is the compound represented by the general formula (6) and, therefore, it can be recovered and recycled to the thermal decomposition step. That is another advantage of the present invention.

In the manufacture of the N-substituted (meth)acryladmide starting from (meth)acrylate as a starting material, a method in which the amine is used as a protecting group may be advantageous in the manufacture of N,N-dialkyl-(meth)acrylamides but, when applied to the manufacture of N-monosubstituted (meth)acrylamides, large quantities of the impurities with high boiling points and high viscosities are detached as mentioned above.

This is because active hydrogens remain in the compound in which a primary amine is added to the double bond of the (meth)acrylate whereby it further adds to another (meth)acrylate to give a compound represented by a general formula (7).

$$R^3(CH_2CHRCOOR')_2 \tag{7}$$

in which R is a hydrogen atom or a methyl group; R' is a lower alkyl group; and $R^3$ is an alkyl group.

When the compound of the general formula (7) is amidated, these (amides) have a high boiling point and a high viscosity and also is hardly decomposed by heating. Thus, when N-monosubstituted beta-amino(methyl)propionamide are subjected to thermal decomposition, the yield decreases.

In the present invention, dialkylamine mixture is initially added to the double bond and, since the beta-dialkylaminopropionate produced thereby has no active hydrogen, it no longer adds to the double bond of the (meth)acrylate whereby neither impurities as by-products nor high-boiling-point products are produced. Consequently, the yield is high and, in addition, polymerization caused by an unnecessary rise of the temperature during the thermal decomposition does not take place.

When two types of amines are used, there is a possibility that an exchange reaction may take place between the amine which is added to the double bond and another amine which is used for the amidation reaction but, as in the case of the present invention, when the amine used for protecting the double bond is dialkylamine while another which is used for the amidation is a primary amine, such an exchange reaction does not take place possibly due to the difference in their reactivities whereby the reaction proceeds with a high yield.

THE BEST MODE FOR CONDUCTING THE INVENTION

EXAMPLE 1

Diethylamine (350 g; 4.8 moles) was added to 344 g (4 moles) of methyl acrylate containing 500 ppm of methoxyhydroquinone and the mixture was made to react at 70°–80° C. for 15 hours, so that the addition to the double bond was completed. After completion of the reaction, the unreacted diethylamine was removed by distillation to give 630 grams of methyl beta-diethylaminopropionate. The yield was 99%.

To this, 15.4 g of 28% methanolic solution of sodium methoxide were added and methylamine gas was introduced into the liquid with a pressure of 0–0.5 kg/cm$^2$G while stirring and keeping the liquid temperature at not higher than 40° C. using a water bath. After three hours, the absorption of the gas ceased, causing the reaction to stop. Concentrated sulfuric acid (3.8 g) was added to the reaction solution to neutralize it, then the salt separated therefrom was filtered off, 0.3 g of phenothiazine as a polymerization inhibitor were added to the filtrate and a low-boiling substances were removed by distilling the mixture to give 620 grams of N-methyl-beta-diethylaminopropionamide. This was analyzed by means of gas chromatography, whereby the purity was found to be 98.5%. Incidentally, the yield from methyl acrylate was 96.6%.

Two hundred grams out of 620 grams of the resulting N-methyl-beta-diethylaminopropionamide was placed in a flask equipped with a distillation column, 1 ml of concentrated sulfuric acid was added thereto and the mixture was heated to 155° C. at 45 torr while stirring. As a result of the thermal decomposition, N-methylacrylamide and diethylamine were produced and, therefore, the top of the fractionating column was kept at 123°–130° C. and the distillated N-methylacrylamide was collected by cooling with a water-cooling condenser. When the amount of the liquid in the flask decreased, the residual N-methyl-beta-diethylaminopropionamide was supplemented thereto and, within seven hours, the total amount was used up, whereby 325 grams of the distillate were obtained.

In the meanwhile, diethylamine was collected by condensing by means of a cooling trap kept at −10° C. to recover 214 grams in which the amount of diethylamine was not less than 99%.

The amount of the liquid remained in the flask (about 20% of N-methyacrylamide and about 70% of N-methyl-beta-diethylaminopropionamide) was 70 grams. It is still fluid and no insoluble matter was found therein.

To all of the above-mentioned distillate was added 0.2 g of phenothiazine, the mixture was distilled at 1.5 torr and a fraction having a boiling point of 67°–69° C. was collected to give 268 grams of N-methylacrylamide. The purity as checked by gas chromatography was 99% and the overall yield was 78%.

The structure of the resulting compound was confirmed by means of NMR and GC-MS analyses.

Comparative Example 1

Methyl acrylate (4 moles; 344 g) was placed in an autoclave and methylamine gas was introduced thereinto by keeping the reaction temperature at not higher than 40° C. by cooling with water so that the addition reaction to the double bond was completed. After two hours, no more absorption of the gas took place and, therefore, the reaction was stopped. According to gas-chromatographic analysis, the rate of conversion of methyl acrylate was 100% while the rate of selectivity of methyl beta-methylaminopropionate was only 18% and the remaining 82% was methyl methylamino-N,N-bispropionate which was produced by further addition with methyl acrylate.

The reaction solution was subjected to an after-treatment in the same manner as in Example 1 and then amidated with methylamine like that in Example 1. Then, 1 molar % of sulfuric acid was added thereto and the mixture was heated at 45 torr to conduct thermal decomposition. However, even when heated at 155° C., no N-methylacrylamide was distilled and, upon further heating left the temperature of the apparatus at 220° C. for seven hours, 88 grams of the distillate was obtained. When the remaining liquid in the flask was cooled down to room temperature, a very viscous tar-like substance was produced.

EXAMPLE 2

To 636 grams (4 moles) of methyl beta-diethylaminopropionate obtained in the same manner as in Example 1 were added 15.4 g of 28% methanolic solution of sodium methoxide and, while stirring, 350.4 g (4.8 moles) of n-butylamine was added thereto. After that addition, the mixture was made to react by keeping the liquid temperature at 70°–80° C. using a water bath to complete the amidation reaction. Then, it was neutralized, desalted, and 0.3 g of phenothiazine were added thereto and the mixture was distilled to remove low-boiling substances whereupon 801 grams (yield: 99.1% ) of N-butyl-beta-diethylaminopropionamide with a purity of 99% as checked by gas chromatography were obtained.

This was then subjected to a thermal decomposition at 45 torr and 180° C. for seven hours in the same manner as in Example 1 to give 468 g of the distillate. The liquid remaining in the flask was fluid and no polymeric component was found.

To all of the above-mentioned distillate, 0.2 g of phenothiazine were added, the mixture was distilled at 1.5 torr and the fraction of 83°–86° C. was collected to give 390 grams of N-butylacrylamide. The purity as checked by gas chromatography was 99% and the overall yield was 76%.

The structure of the resulting compound was confirmed by means of NMR and GC-MS analyses.

Comparative Example 2

Methyl acrylate (344 g; 4 moles) was placed in a flask and 642.4 g (8.8 moles) of n-butylamine were added thereto while stirring by cooling with water to keep it at not higher than 50° C. After two hours, the addition reaction was complete but an impurity, namely butoxyamine-N,N-bis-3-propionic acid methyl ester, was produced in an amount of about 12% in terms of the ratio of the area of its peak that of to methyl beta-butylaminopropionate on a gas chromatogram.

Then 15.4 g of 28% methanolic solution of sodium methoxide were added to the reaction solution and the amidation reaction was continued at 70°–80° C. for four hours. After completion of the reaction, the mixture was neutralized, desalted, 0.3 g of phenothiazine was added thereto and the mixture was distilled to evaporate the low-boiling substances whereupon 780 g of N-butyl-beta-butylaminopropionamide with a purity of 86% as checked by gas chromatography were obtained.

The resulting amide was subjected to the same thermal decomposition as in Example 2. However, no thermal decomposition took plac at 180° C. and a temperature of 200° C. or higher was needed. Also, as the thermal decomposition proceeded, the temperature of the liquid rose and, after seven hours when the amount of the distillate became 236 grams, the thermal decomposition had to be stopped.

The distillate of the thermal decomposition was purified by distillation, 178 grams of n-butylacrylamide was obtained. The overall yield was 35%.

EXAMPLE 3

Methanol (128 g) was added to 344 g (4 moles) of methyl acrylate containing 500 ppm of methoxyhydroquinone and, while stirring and placed in a water bath, 404 g (4 moles) of dipropylamine was added dropwise thereinto over a period of 30 minutes. After completion of the dropping, the reaction was continued at 70° C. for three hours. After completion of the reaction, methanol was evaporated therefrom to give 746 g of methyl beta-dipropylaminopropionate. The purity as checked by gas chromatography was 99%.

To this were added 15.4 g of 28% methanolic solution of sodium methoxide and 619 g (4.8 moles) of 2-ethylhexylamine, and an amidation reaction was carried out at 80° C. for four hours. After completion of the reaction, the mixture was neutralized, desalted, 0.3 g of phenothiazine was added and low-boiling substances were removed therefrom by distillation to give 1,131 grams of N-2-ethylhexyl-beta-dipropylaminopropionamide. The yield from methyl acrylate was 97.8% and the purity as checked by gas chromatography was 98.2%.

This was then subjected to thermal decomposition at 13 torr and 190° C. for ten hours in the same manner as in Example 1 to give 590 grams of the distillate.

Phenothiazine (0.2 g) was added to the distillate, the mixture was distilled at 2 torr and the fraction of 133°–138° C. was collected to give 502 grams of N-2-ethylhexylacrylamide. The purity as checked by gas chromatography was 98.4% and the overall yield was 67.5%.

The structure of the resulting compound was confirmed by means of NMR and by GC-MS analyses.

Comparative Example 3

The same addition and amidation reactions as in Comparative Example 2 were carried out with the exception that 8.8 moles of 2-ethylhexylamine were used in place of n-butylamine and the low-boiling substances were removed by distillation to give a crude N-2-ethylhexyl-beta-dipropylaminopropionamide. This contained about 9% of high-boiling-point impurities.

To this was added sulfuric acid, the mixture was subjected to thermal decomposition at 13 torr at 210° C. and the resulting distillate was distilled to give 301 grams of N-2-ethylhexylacrylamide. The purity as checked by gas chromatography was 98.7% and the overall yield was 41%.

EXAMPLE 4

Methanol (128 g; 4 moles) was added to 344 g (4 moles) of methyl acrylate containing 500 ppm of methoxyhydroquinone and 404 g (4 moles) of dipropylamine were added dropwise thereinto while placed in a water bath and stirred for a period of 30 minutes. After completion of the addition, the temperature of the liquid was raised to 70° C. and the reaction was carried out for three hours. After completion of the reaction, methanol was removed by distillation to give 746 grams of methyl beta-dipropylaminopropionate with a purity of 99%.

To this were added 15.4 g of 28% methanolic solution of sodium methoxide and the amidation reaction was carried out at 80° C. for four hours after the addition of 490 g (4.8 moles) of dimethylaminopropylamine. After completion of the reaction, the mixture was neutralized, desalted, 0.3 g of phenothiazine was added and the low-boiling-point substances were removed by distillation to give 1,025 grams of N-dimethylaminopropyl-beta-dipropylaminopropionamide. The purity as checked by gas chromatography was 98.6% and the yield was 98.5%.

The resulting amide was subjected to thermal decomposition in the same manner as in Example 1 at 13 torr and 190° C. for nine hours to give 535 g of the distillate. The residue in the flask was still fluid and no insoluble matter was found therein.

Phenothiazine (0.2 g) was added to all of the above distillate, the mixture was distilled at 2 torr and the fraction of 113°–117° C. was collected to give 458 grams of N-dimethylaminopropylacrylamide. The purity was 98.6% and the overall yield was 72.3%.

The structure of the resulting compound was confirmed by means of NMR and GC-MS analyses.

Comparative Example 4

To 4 moles of methyl acrylate were added 8.8 moles of dimethylaminopropylamine and the mixture was subjected to an addition reaction in the same manner as in Comparative Example 2. Then sodium methoxide was added thereto to conduct the amidation reaction. After completion of the reaction, the low-boiling-point substances were removed by distillation to give a crude N-dimethylaminopropyl-beta-dimethylaminopropylaminopropionamide. This contained about 13% of high-boiling-point impurities.

To this was added sulfuric acid and the mixture was subjected to thermal decomposition at 210° C. However, during the reaction, the boiling point rose and, also, the thermal decomposition rate became very slow.

The distillate, following thermal decomposition, was distilled to give 168 grams of N-dimethylaminopropylacrylamide with a purity of 99% as checked by gas chromatography. The overall yield was 27%.

EXAMPLE 5

To 746 g of methyl beta-dipropylaminopropionate which was prepared in the same manner as in Example 4 were added 15.4 g of 28% methanolic solution of sodium methoxide, then 293 g (4.8 moles) of ethanolamine were added dropwise thereinto and the mixture was made to react at 70° C. for one hour. After completion of the reaction, the mixture was neutralized, desalted, 0.3 g of phenothiazine were added thereto and the low-boiling-point substances were removed by distillation to give 858 grams of N-hydroxyethyl-beta-dipropylaminopropionamide. The purity as checked by gas chromatography was 98% and the yield was 97.3%.

To 200 g of the above-prepared amide was added 1 ml of concentrated sulfuric acid, the mixture was subjected to thermal decomposition at 10 torr and 180° C. and the reaction was continued for nine hours while by supplying the amide, if the liquid in the apparatus decreased, whereupon 375 g of the distillate were obtained.

The distillate was distilled at 1 torr and, as a fraction of 140° C., 313 grams of N-hydroxyethylacrylamide were prepared. The purity as checked by gas chromatography was 98% and the overall yield was 67%.

Comparative Example 5

The same addition and amidation reactions as in Comparative Example 2 were carried out with the exception that 8.8 moles of ethanolamine were used in place of n-butylamine. After neutralization and desalting, the low-boiling-point substances were removed by distillation.

The product was a very viscous liquid and, though it was attempted to subject it to a thermal decomposition at 10 torr, no decomposition took place at all even when the liquid temperature was raised to 220° C. whereby none of the desired products was obtained.

EXAMPLE 6

128 g of methanol was added to 400 g (4 moles) of methyl methacrylate containing 500 ppm of methoxyhydroquinone, 344 g (4 moles) of diethylamine were added thereto by keeping the liquid temperature at 60° C. and the reaction was carried out at 60° C. for five hours. After completion of the reaction, methanol was evaporated therefrom to give 690 grams of methyl beta-diethylamino(1-methyl)propionate with a purity of 99%.

To this were added 15.4 g of 28% methanolic solution of sodium methoxide, methylamine gas was introduced thereinto in an autoclave at 40° C. and 0–0.5 kg/cm² for five hours and the amidation reaction was carried out. After completion of the amidation reaction, the mixture was neutralized, desalted, 0.3 g of phenothiazine were added, the low-boiling-point substances were removed by distillation and 685 grams of N-methyl-beta-diethylamino(1-methyl)propionamide were obtained. The yield from methyl methacrylate was 97.8% and the purity as checked by gas chromatography was 98.2%.

This was then subjected to thermal decomposition at 45 torr and 155° C. in the same manner as in Example 1 to give 340 g of the distillate.

Phenothiazine (0.2 g) was added to the above distillate, the mixture was distilled at 1.5 torr and the fraction of 75°–80° C. was collected to give 276 grams of N-methyl-methacrylamide. The purity as checked by gas chromatography was 98.8% and the overall yield was 69%.

Comparative Example 6

Methyl methacrylate (400 g) was placed into an autoclave and then methylamine gas was introduced thereinto at 40° C. and 0–0.5 kg/cm² for five hours.

After completion of the reaction, the reaction solution was analyzed by means of gas chromatography whereupon impurities were found to be present in a ratio of about 30% in addition to of the area of the peaks N-methyl-beta-diethylamino(1-methyl)propionamide.

INDUSTRIAL APPLICABILITY

As fully illustrated hereinabove, a specific dialkylamine is initially added to the double bond of the acryl group in (meth)acrylate and then a reaction for the formation of an amide is carried out in accordance with the thermal decomposition whereupon N-monosubstituted (meth)acrylamide can be manufactured at a high yield and in an industrially-advantageous manner without the production of any side products at all.

What is claimed is:

1. A method of manufacturing N-monosubstituted (meth)-acrylamide represented by formula (I):

$$CH_2=CRCO-NHQ \qquad (I)$$

in which R is a hydrogen atom or methyl and Q is an alkyl having 1–12 carbons, a dimethylaminoalkyl having 1–5 carbons or a hydroxyalkyl having 1–3 carbons, characterized in that (1) (meth)acrylate represented by formula (II):

$$CH_2=CRCOOR' \qquad (II)$$

in which R is a hydrogen atom or methyl and R' is a lower alkyl, is made to react with dialkylamine represented by formula (III):

$$R^1R^2NH \qquad (III)$$

in which $R^1$ and $R^2$ are lower alkyls;

(2) the resulting beta-dialkylamino(1-methyl)propionate represented by formula (IV):

$$R^1R^2N-CH_2-CHRCOOR' \qquad (IV)$$

in which R is a hydrogen atom or methyl; R' is a lower alkyl; and $R^1$ and $R^2$ are lower alkyls, is made to react, in the presence of an alkali metal alkoxide, with a primary amine represented by formula (V):

$$NH_2-Q \qquad (V)$$

in which Q is an alkyl having 1–12 carbons, a dimethylaminoalkyl having 1–5 carbons or a hydroxyalkyl having 1–3 carbons; and (3) the resulting N-monosubstituted beta-dialkylamino(1-methyl)propionamide represented by formula (VI):

$$R^1R^2N-CH_2-CHRCO-NHQ \qquad (VI)$$

in which R is a hydrogen atom or methyl; $R^1$ and $R^2$ are lower alkyls; and Q is an alkyl having 1–12 carbons, a dimethylaminoalkyl having 1–5 carbons or a hydroxyalkyl having 1–3 carbons, is subjected to thermal decomposition.

2. A method of manufacturing N-monosubstituted (meth)-acrylamide as claimed in claim 1, wherein the (meth)acrylate ester represented by formula (II) is a methyl ester.

3. A method of manufacturing N-monosubstituted (meth)-acrylamide as claimed in claim 1, wherein the dialkylamine represented by formula (III) is diethylamine or dipropylamine.

4. A method of manufacturing N-monosubstituted (meth)-acrylamide as claimed in claim 1, which is characterized by adding an alcohol when the acryl ester represented by formula (II) is made to react with the dialkylamine represented by formula (III).

5. A method of manufacturing N-monosubstituted (meth)-acrylamide as claimed in claim 1, which is characterized by adding 0.5 to 2 molar % of sulfuric acid to the amide represented by formula (VI) as a catalyst during the thermal decomposition.

6. A method of manufacturing N-monosubstituted (meth)-acrylamide as claimed in claim 1, wherein said thermal decomposition is conducted at a temperature of from 100° to 200° C.

7. A method of manufacturing N-monosubstituted (meth)-acrylamide as claimed in claim 1, wherein said thermal decomposition is conducted under a pressure of from 10 to 200 Torr.

* * * * *